United States Patent
Kindlein et al.

(10) Patent No.: US 8,559,598 B2
(45) Date of Patent: Oct. 15, 2013

(54) MINIATURE X-RAY SOURCE DEVICE FOR EFFECTING RADIATION THERAPY

(75) Inventors: Johann Kindlein, Adendorf (DE); Evert Hendrik Agterhuis, Loenhout (BE); Godefridus Hendricus Maria Gubbels, Helmond (NL); Frank Simonis, Oirschot (NL)

(73) Assignee: Nucletron B.V., Veenendaal (NL)

( * ) Notice: Subject to any disclaimer, the term of this patent is extended or adjusted under 35 U.S.C. 154(b) by 420 days.

(21) Appl. No.: 12/665,491

(22) PCT Filed: Jun. 17, 2008

(86) PCT No.: PCT/EP2008/004860
§ 371 (c)(1),
(2), (4) Date: Jun. 7, 2010

(87) PCT Pub. No.: WO2008/155092
PCT Pub. Date: Dec. 24, 2008

(65) Prior Publication Data
US 2010/0246766 A1    Sep. 30, 2010

Related U.S. Application Data

(60) Provisional application No. 60/945,029, filed on Jun. 19, 2007.

(30) Foreign Application Priority Data

Jun. 19, 2007   (EP) .................................... 07011953

(51) Int. Cl.
*H01J 35/00*    (2006.01)

(52) U.S. Cl.
USPC ............................. 378/121; 378/143; 378/65

(58) Field of Classification Search
USPC ................... 378/65, 119, 121, 122, 140, 143
See application file for complete search history.

(56) References Cited

U.S. PATENT DOCUMENTS

| | | | |
|---|---|---|---|
| 6,324,257 B1 | 11/2001 | Halavee | 378/121 |
| 6,480,573 B1 | 11/2002 | Dinsmore | 378/136 |
| 6,771,737 B2 * | 8/2004 | Kerslick et al. | 378/122 |
| 2006/0060793 A1 | 3/2006 | Lewellen et al. | 250/492.1 |

* cited by examiner

*Primary Examiner* — Courtney Thomas
(74) *Attorney, Agent, or Firm* — Finnegan, Henderson, Farabow, Garrett & Dunner LLP (57) ABSTRACT

A miniature X-ray source device for effecting radiation therapy at least comprising a vacuum tube containing a cathode and an anode spaced apart at some distance from each other; emitting means for emitting free electrons from the cathode; electric field generating means for applying during use a high-voltage electric field between the cathode and the anode for accelerating the emitted free electrons towards the anode, as well as an exit window for X-ray radiation being generating at the anode. The present invention provides an improved miniature X-ray source device, that can also properly be used in treating skin cancer and which is easy to handle. The anode is provided with a flat X-ray emitting surface. In particular, the cathode exhibits a concave shaped surface having a center part surrounded by an upright circumferential edge, wherein the center part of the concave shaped surface is provided with an electron emitting material.

27 Claims, 6 Drawing Sheets

MINIATURE X-RAY SOURCE DEVICE FOR EFFECTING RADIATION THERAPY

CROSS-REFERENCE TO RELATED APPLICATIONS

This application is a U.S. national stage application under 35 U.S.C. § 371 of International Application No. PCT/EP2008/004860, filed Jun. 17, 2008, which claims priority to U.S. Provisional Application No. 60/945,029, filed Jun. 19, 2007, and European Application No. 07011953.2, filed Jun. 19, 2007, the content of all of which are incorporated herein by reference.

The invention relates to a miniature X-ray source device for effecting radiation therapy at least comprising a vacuum tube containing a cathode and an anode spaced apart at some distance from each other; emitting means for emitting free electrons from the cathode; electric field generating means for applying during use a high-voltage electric field between the cathode and the anode for accelerating the emitted free electrons towards the anode, as well as an exit window for X-ray radiation being generating at the anode.

The invention also relates to a method for performing radiation therapy treatment on an anatomical portion of an animal body using a miniature X-ray source device.

Radiation therapy is a well-established method for treatment of several diseases, including cancer. The presumptive usefulness of a miniature X-ray source device is clear. The insertion of such a source device into vessels or other body cavities would allow the delivered radiation dose to be confined to a small tissue region. More specific, a catheter with a miniaturized X-ray source device could be used for irradiation of cardiovascular tissue.

In a known embodiment a miniature X-ray source device according to the state of the art comprises a vacuum tube, wherein a cathode and an anode spaced apart are accommodated. The anode is mounted on a distal end of the miniature X-ray source device. The vacuum tube is to be evacuated to a preferred vacuum level required for a proper operation of the miniature X-ray source device. Furthermore, the known miniature X-ray source device is provided with electric field means for establishing a high-voltage electric field between the anode and cathode. Electrons emitted from the cathode are accelerated by the established high-voltage electric field and impact with a high kinetic energy on the anode material. In the anode material X-ray radiation is generated with a high energy level.

As the vacuum tube is entirely highly transparent to X-ray radiation, the generated radiation can leave the vacuum tube towards the patient's tissue in which the X-ray source device is inserted. As the generated X-ray radiation leaving the miniature X-ray source device exhibits a high energy level, the X-ray radiation is highly suitable for performing radiation therapy in the patient's body, for example for treating cancer tumours.

Although the known miniature X-ray source devices are highly suitable for performing radiation therapy treatment in a patient's body, X-ray radiation is also the main type of radiation used for the treatment of skin cancers. Low energy X-rays (less than 90 kV) do not penetrate very deep into the body tissue. Those rays transmit most of their energy into the skin and are therefore used for the treatment of skin cancers. For such a skin cancer treatment the dose of radiation to be delivered is fractionated. For most skin cancers a total of 10-25 fractions are administered, wherein the radiation therapy is administered by specially trained radiation therapist and each fraction usually takes 15-20 minutes. The subsequent fractions are usually given on daily basis (Monday-Friday) and a full treatment course can take 2-5 weeks to complete.

However the X-ray radiation being used till now are of a low energy level. The continuous technological advances creates in the field of brachytherapy have made possible the use of highly accurate afterloading equipment for skin cancer treatments. The minimum dose administered to the tumor is 60-65 Gy during 33-36 fractions at 0.18 Gy/fraction. High Dose Rate (HDR) brachytherapy is therefore a reasonable alternative to other therapy techniques for the treatment of skin carcinomas. However, as a disadvantage the use of HDR brachytherapy not applicable on a large basis.

Radiation treatments using HDR Ir-192 sources are limited to the radiotherapy centers, which use this technology. Furthermore conventional X-ray devices are expensive and not easy to handle, whereas also the dosimetry characteristics are complicate and not reproducible.

It is an object of the present invention to provide an improved miniature X-ray source device, that can also properly be used in treating skin cancer and which are easy to handle. According to the invention the cathode exhibits a concave shaped surface having a center part surrounded by an upright circumferential edge, wherein the center part of the concave shaped surface is provided with an electron emitting material.

Preferably the center part of the concave shaped surface has a flat configuration.

In another embodiment the cathode is of a cold cathode type formed from carbon nanotubes. In the embodiment wherein the cathode is a so-called cold cathode type formed from carbon nanotubes, carbon nanotubes are aligned mono-wall nanotubes or carbon nanotubes are aligned multi-wall nanotubes. In both embodiments the carbon nanotubes may be randomised nanotubes.

According to a further embodiment of the X-ray source device according to the invention a getter material is located in a high-voltage electric field free region in the vacuum tube. An essentially electric field free location of the getter material is required as therefore the getter would not present any internal electrical problems associated with surface arcing or breakdown. Also the use of a getter material inside the vacuum tube improves the vacuum level inside.

In a specific embodiment the getter material is positioned within a groove present on the cathode. With this feature it is possible to position the getter material inside the vacuum tube in a such way, wherein it is shielded from the high-voltage electric field by means of the cathode. A significant reduction in the constructional dimensions is thus obtained, allowing a further miniaturisation of the known miniature X-ray source device thus further improving the positioning of such X-ray source device relative to the patient's body.

According to another beneficial embodiment the anode is provided with a flat X-ray emitting surface making the device highly suitable in the treatment of skin cancers.

More in particular the anode is made from a first material, which material is at least partly transparent to X-ray radiation and wherein the anode is covered with a layer of a second material, which second material is at least partly non-transparent to X-ray radiation.

Preferably the second material is for example tungsten.

In another preferred embodiment the layer of the second material has a thickness between 10 and 60 µm and preferably approximately 20 µm.

An additional control of the bundle characteristics of the X-ray radiation being emitted from the anode can be achieved as according to a further embodiment within the vacuum tube a diaphragm lens element is disposed between the cathode and the anode for bundling the electrons being emitted towards the anode.

In order to allow a proper control or adaptation of the geometrical bundle characteristics of the electron bundle or beam towards the anode the diaphragm lens element is electrically controllable.

The operation of the miniature X-ray source device is not adversely affected as within the vacuum tube a grid shaped electron absorbing element is disposed between the cathode and the diaphragm lens element for absorbing any electrons being reflected from the diaphragm lens element towards the cathode. By absorbing electrons being reflected from the diaphragm lens element the cathode is being protected from impinging electrons.

A further enhanced control of the bundle characteristics of the X-ray radiation being emitted from the anode is possible as according to a beneficial further embodiment the anode is displaceably accommodated within the X-ray source device with respect to the exit window.

Furthermore it is preferred that the vacuum tube is at least partly made from an electrically isolating material and more in particular it is preferred that the electrically isolating material is coated with a polymer layer. This gradually reduces the voltage difference existing between the cathode and the anode (which is normally kept at ground potential), thereby enhancing the performance of the X-ray source device.

Preferably the X-ray source device has a cylindrical shape with a diameter of 1-2.5 mm and a length of 2-3 cm.

In order to improve the heat dissipation of the anode due to the electrons impinging on the anode surface material, the X-ray source device comprises cooling means for cooling at least the anode.

In a further preferred embodiment the source device is mounted using a movable robotic arm of a therapy treatment system, the movement of the robotic arm being controlled by information generated by imaging means and therapy treatment planning means of the therapy treatment system. This allows complex radiation treatment sessions to be performed, wherein the positioning of the source device and the radiation dose to be delivered requires an accurate and reproducible control.

The imaging means may comprise a laserscanning device.

The invention will now be described or in more detail with reference to a drawing which drawing shows in.

In the following detailed description with reference to the accompanying figures identical components of the embodiments shown will be indicated with identical reference numerals.

Figure 1:
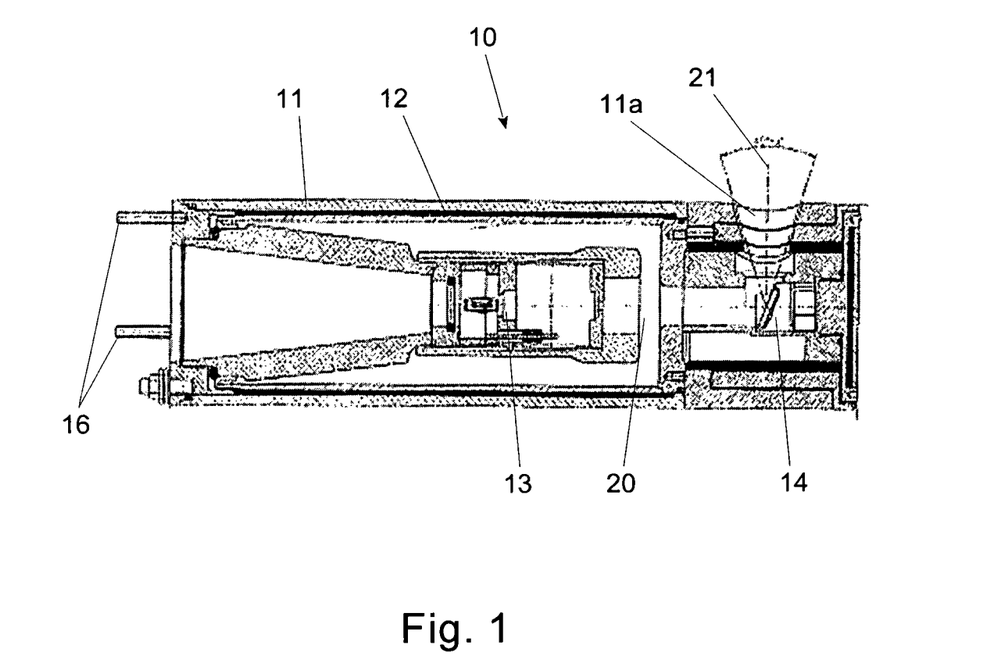
FIG. 1 an embodiment of a miniature X-ray source device according to the state of the art.

In FIG. 1 a known miniature X-ray source device according to the state of the art is disclosed showing the miniature X-ray source device 10 in a longitudinal cross-section. The miniature X-ray source device 10 according to the prior art comprises a housing 11 with an exit window 11a for the X-ray radiation being generated. Within the housing 11 a vacuum tube or chamber 12 is accommodated containing an cathode 13 and an anode 14 spaced apart from each other within space 20 of the vacuum tube 11.

The cathode material 14 consist of an electron emitting material from which electrons are freed using techniques already known in the art.

In general a known miniature X-ray source device according to the state of the art is further provided with means 16 for establishing a high-voltage electric field between the anode 14 and cathode 13. To this end the cathode 13 is connected with an supply wire connected with a high-voltage source, whereas the anode 14 is kept at ground potential.

The electrons freed from said cathode material 13 are accelerated by said high-voltage electric field and impact on the anode material 14. Due to the high velocity of the electrons specific X-ray radiation 21 is generated within the anode material 14. The X-ray radiation 21 will escape the vacuum tube 11 via the exit windows 11a towards the tissue of the patient in which the miniature X-ray source device is implanted due to the fact that the exit window 11a is manufactured from a material which is highly transparent for X-ray radiation.

As stated in the introduction of this patent application the radiation dose distribution thus generated is not always applicable for certain radiation therapy treatments, for example brachytherapy.

Figure 2:
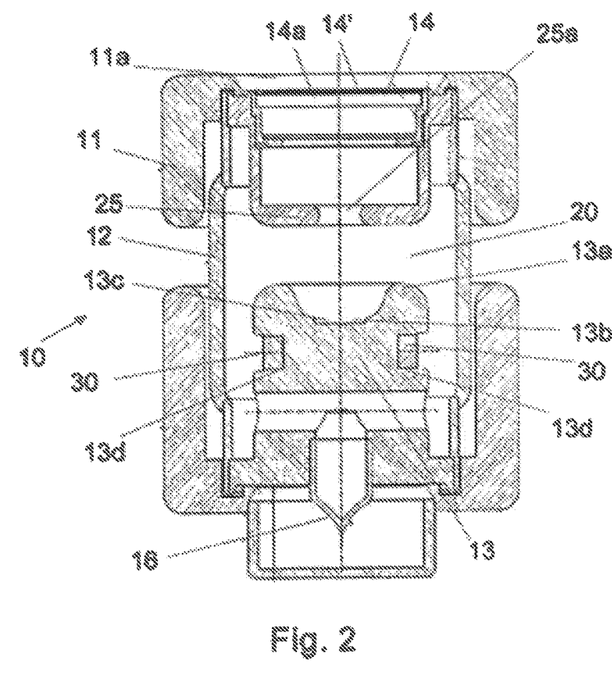
FIG. 2 a first embodiment of a miniature X-ray source device according to the invention.

The embodiment of the miniature X-ray source device of FIG. 2 is provided with an anode 14 which is provided with a flat X-ray emitting surface. The flat X-ray emitting surface 14a of the anode 14 allows a proper handling of the miniature X-ray source device 10 especially for the treatment of skin cancer. To this end the X-ray source device 10 has to be placed with the exit window 11a on or in close proximity to the skin of the patient to be treated in order to direct the X-ray radiation generated within the flat anode 14 towards the skin and the intended site to be treated.

Preferably the anode 14 is made from a first material, which material is at least partly transparent to X-ray radiation and wherein the anode is covered with a layer of a second material (schematically depicted with the thick line 14') which second material 14' is at least partly non-transparent to X-ray radiation. Preferably said second material 14' is for example made from tungsten, wherein the layer of the second material has a thickness between 10 and 50 µm and preferably approximately 20 µm.

The cathode 13 exhibits an concave shaped surface consisting of an upright circumferential edge 13a surrounding a center part 13b. The center part 13b has preferably a flat configuration and is according to the invention provided with an electron emitting material 13c.

The electron emitting material 13c of the cathode 13 is preferably of a cold cathode type formed from carbon nanotubes, which are preferably aligned mono-wall nanotubes. Another embodiment the carbon nanotubes are aligned multiwall nanotubes. In both embodiments it is also possible to use randomized nanotubes.

It is also possible to position a getter material 30 within the vacuum chamber 12. The getter material 30 is electrically isolated accommodated within the vacuum tube 12 (space 20) and serves to eliminate or capture stray gas molecules still present within the cavity 20 of the vacuum tube 12. Therefore the use of a getter material 30 guarantees a low vacuum level within the vacuum tube 12 necessary for a proper operation of the miniature X-ray source device according to the invention.

As shown in FIG. 2 the cathode 13 is provided with a space or groove 13d in which the getter material 30 is accommodated. Optionally said groove or space 30 is circumferentially provided in the cathode.

In order to control the bundle characteristics of the X-ray radiation 21 being emitted from the anode 14 a diaphragm lens element 25 is disposed between the cathode 13 and the anode 14. The diaphragm lens element 25 is provided with an opening 25a intended to bundle the electrons being emitted from the cathode 13 as an oriented bundle towards the anode 14. The diaphragm lens element 25 can be electrically controllable in order to manipulate the specific geometrical bundle characteristics of the electron current of free electrons towards the anode 14.

In order to avoid a possible distortion of the operation of the X-ray source device 10 due to free electrons being reflected from the diaphragm lens element 25 back towards the cathode 13 a grid shaped electron absorbing element 26 (see FIGS. 3a-3b) is disposed between the cathode 13 and the anode 14 for absorbing any electrons being reflected. By absorbing these reflected free electrons on the electron absorbing element 26, the cathode 13 is protected from impinging electrons thereon. Moreover with the use of a grid 26 the flexibility of the X-ray source device 10 is increased. The use of a grid element 26 makes it possible to change the electron current between the cathode and the anode through the vacuum tube 12 at a constant acceleration voltage being applied by the electron freeing means 16. This allows the X-ray radiation dose being emitted to be changed and altered effectively.

Preferably the vacuum tube 12 is made from an electrically isolating material covered with a polymer layer. The polymer coating layer can be for example be of the material green Pyrotek TS-207, which coating source to gradually reduce the voltage difference between the cathode 13 and the anode 14.

The exit window 11a (not depicted) which covers the flat shaped anode 14 can be made from $Al_2O_3$/W or Be/W. Also in this embodiment the anode 14 is kept at ground potential.

Although the opening 25a of the diaphragm lens element 25 has a circular shape other configurations are possible depending on the desired bundle characteristic of the electron current inpinching on the anode 14. The opening 25 can be for example square or polygonal.

Figure 3A:
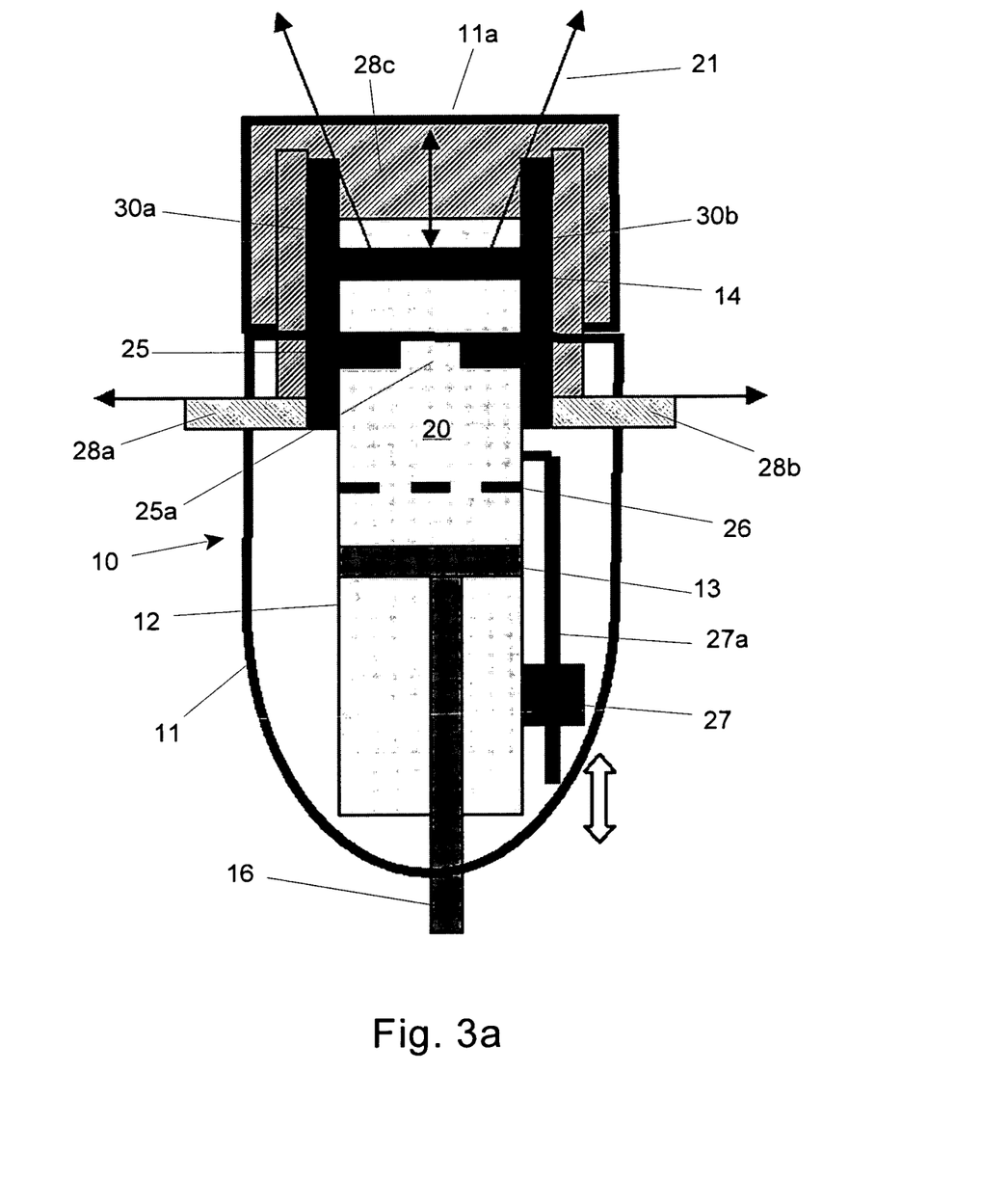
FIGS. 3a-3b a second embodiment of a miniature X-ray source device according to the invention.
Figure 3B:
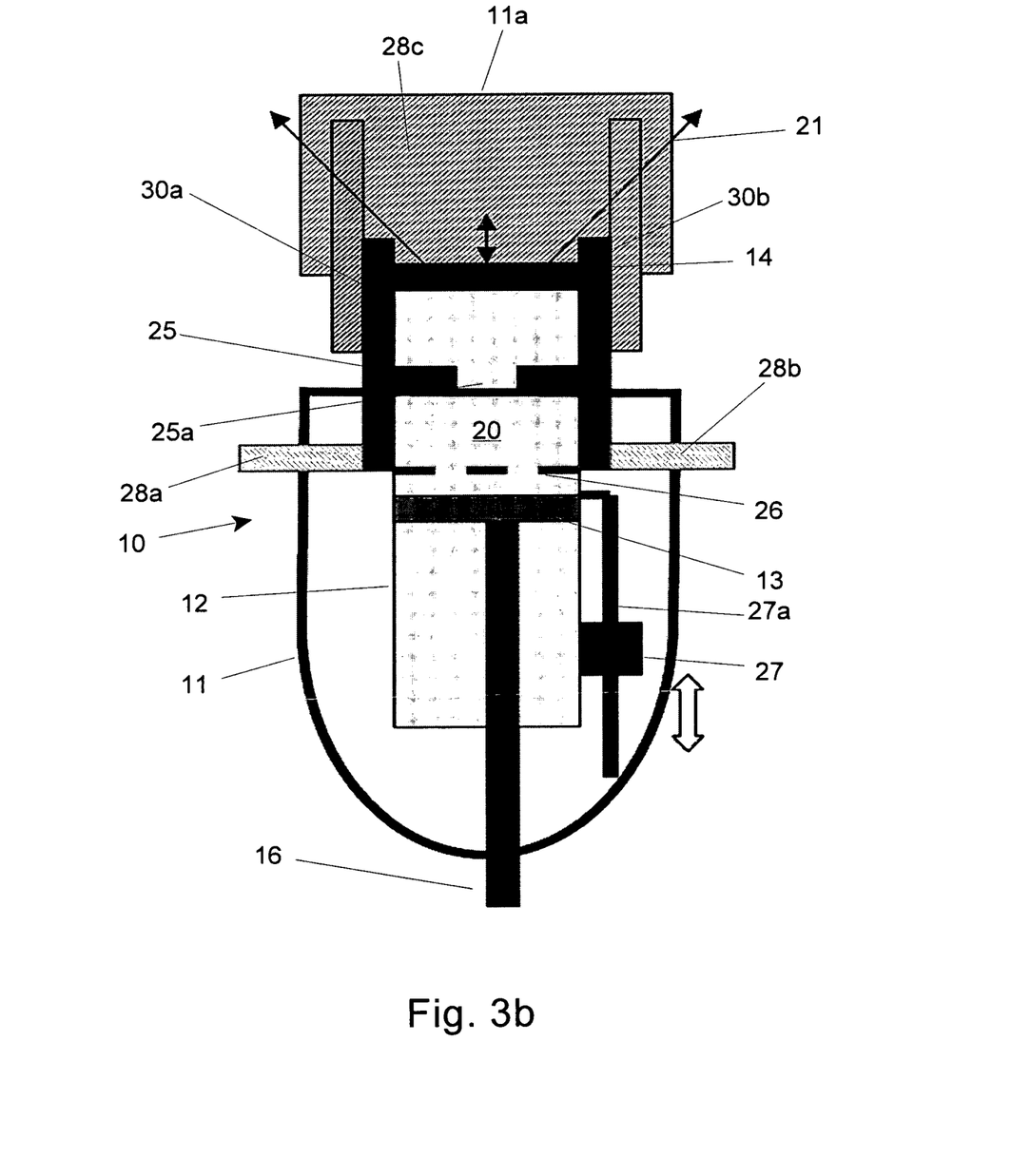

In the FIGS. 3a-3b another embodiment is depicted showing not only the electron absorbing grid element 26 for absorbing any free electrons being reflected back towards the cathode 13 from the diaphragm lens element 25, the X-ray source device 10 as depicted in these figures is also provided with cooling means for cooling the anode. The cooling means comprise an inlet 28a for the entry of a coolant medium (for example water or oil) towards cooling chamber 28c where it is in direct or indirect contact with the anode 14. The coolant medium 29 leaves the X-ray source device 10 via the outlet opening 28b.

The embodiment of FIGS. 3a and 3b disclose a further feature used to modify the bundle characteristics of the X-ray radiation 21 being emitted by the anode 14. The vacuum tube and more in particular the anode 14 is displaceable accommodated within the housing 11 of the miniature X-ray source 10. For displacing the vacuum tube 12 together with the anode 14 proper displacement means 27 are present. The displacement means 27 can be for example a spindle drive motor which advances and retracts a spindle 27 being connected with the vacuum tube 12. However also other displacement means are considered possible and known in the art for example a transmission of gears wherein the teeth mesh with each other.

In FIG. 3a the vacuum tube 12 is displaced in such manner that the anode 14 is positioned at a relatively short distance from the exit window 11a. Adjacent to the anode 14 radiation shielding walls 30a-30b are accommodated within the housing 11 which radiation shielding walls serve as collimating elements modifying the outer dimensions of the X-ray radiation bundle 21 being emitted by the anode 14.

In FIG. 3b the vacuum tube 12 is displaced by the displacement means 27 in such a manner that a X-ray radiation beam 21 is emitted having a larger (read:wider) bundle dimension.

Figure 4:
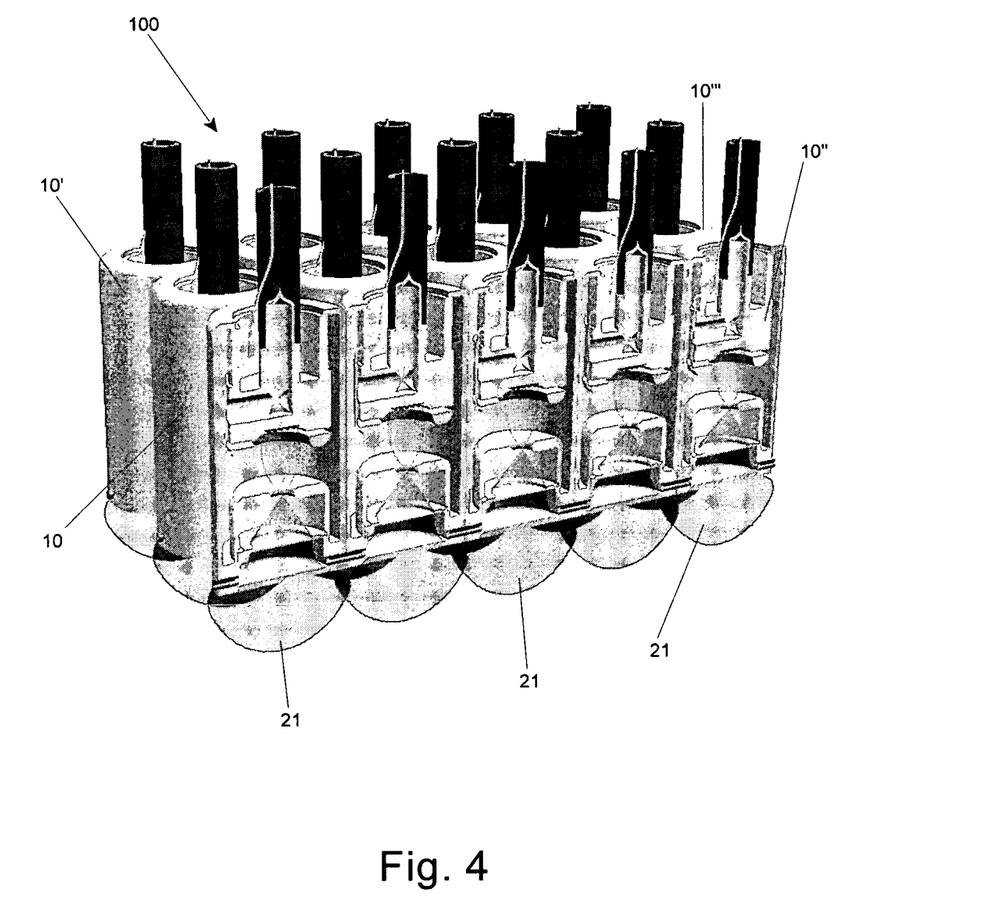
FIG. 4 a radiation assembly composed of an array of miniature X-ray source devices according to the invention.

In FIG. 4 an assembly 100 of multiple miniature X-ray source devices is disclosed. The assembly 100 is composed of multiple miniature X-ray source devices 10-10'-10"-etc.-etc. which miniature X-ray source devices upon activation emit several, individual bundles 21 of X-ray radiation. The assembly 100 allows radiation treatment sessions to be performed when large skin surface area are to be irradiated.

Figure 5:
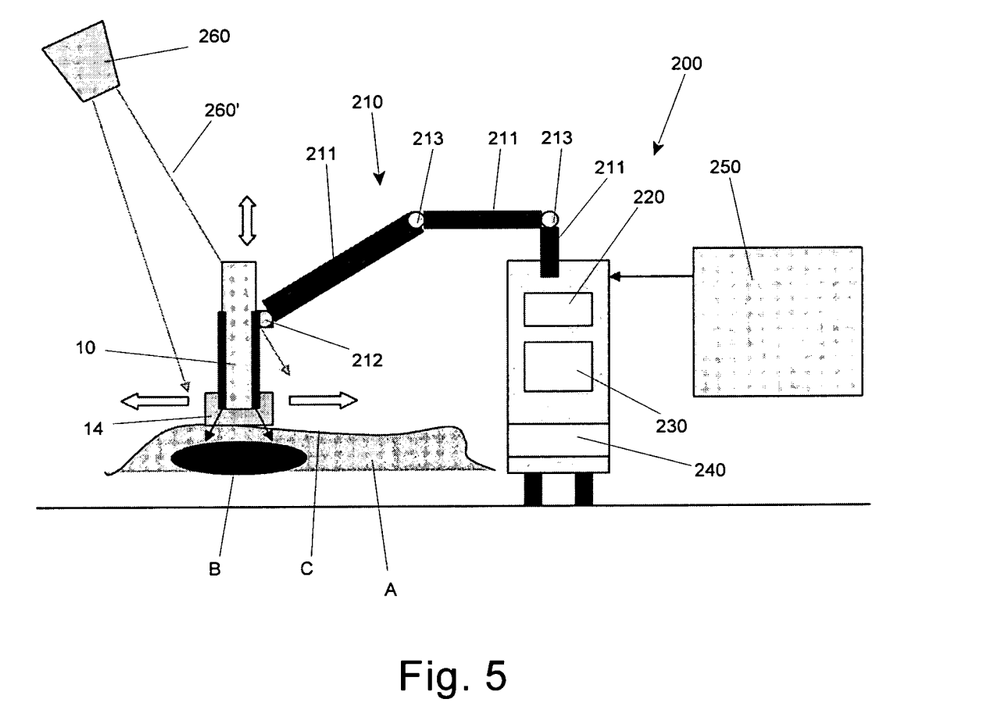
FIG. 5 a radiation treatment system provided with a miniature X-ray source device according to the invention.

In FIG. 5 a radiation therapy treatment apparatus 200 is disclosed comprising a treatment planning unit 250 as well as a high voltage source 220, a coolant generating means 230 and drive means 240 for driving or manipulating a robot arm 210 provided with a connector 212, to which a miniature X-ray source device 10 according to the invention can be mounted. The robotic arm 210 is build up of several segments 211 interconnected by means of hinging elements 213. Through the robotic arm 210 an electric signal conductor is guided for connecting the miniature X-ray source device 10 and especially the electron freeing means 16 (not depicted but shown in FIGS. 2-4a-4b) with the high voltage source 220.

Also a coolant guide tube (not shown) is mounted through the robotic arm 210 towards the cooling means 28a-28c (see other figures) for cooling down the anode 14. The displacement of the robotic arm 10 using the robotic drive means 240 allows a proper and accurate displacement of the miniature X-ray source device 10 across the skin C of a patient A above an intended treatment side B (for example a cancerous tumour to be treated with X-ray radiation).

The displacement of the robotic arm 210 and the miniature X-ray source device 10 using the robotic drive means 240 with respect to the tumour B is controlled based on treatment planning parameters generated by the treatment planning module 250 and image information 260' generated by imaging means 260. The imaging means 260 can be for example a laser scanner and monitors the actual position and orientation of the miniature X-ray source device 10 with respect to the skin C and the intended radiation treatment sight B of the patient A. The actual imaged position of the miniature X-ray source device 10 is in real time monitored and compared with preplanned position information contained in the treatment planning module 250 and the course of displacement of the miniature X-ray radiation source device 10 is instantly adapted based on any observed deviation.

With a treatment apparatus 200 as shown in FIG. 5 the robotic arm 210 can be manipulated as such manner that large skin surface areas can be treated with X-ray radiation emitted by one single miniature X-ray source device 10.

With the treatment apparatus 200 as shown in FIG. 5 the method for performing radiation therapy treatment on an anatomical portion B of an animal body A can be performed using a miniature X-ray source device according to the invention.

According to the invention with the method first comprises the step of obtaining one or more three-dimensional images of the skin surface near said anatomical portion using imaging means 260, which can be a laser scanning device. Said three-dimensional image of said target volume can be displayed to an user using displaying means (not shown).

Based on the three-dimensional image information being obtained the exact location of said anatomical portion is determined. This can be a tumour located at some distance/depth under the skin surface or it can be a cancerous area of skin cancer. According to the invention the three-dimensional images of the skin surface can be obtained by placing/using one or more marker elements on the skin surface.

Using treatment planning means 250 a radiation treatment plan is generated for effecting said radiation therapy. The treatment planning means 250 contain processing means, which can be a computer on which a treatment planning software module is running. Said treatment plan may include information concerning the overall amount of radiation dose to be administered or applied to the anatomical portion, and one or more target locations within the anatomical portion to be treated. Also for each target location the partial dose distribution as well as the dwell time (the duration of the radiation for that target location) is determined.

The treatment plan as generated by the treatment planning means 250 contain information about the position in which the miniature X-ray source device has to be positioned relative to each target location. This position information also contains planning information concerning the distance of the miniature X-ray source device relative to the skin surface for each position.

Also this distance information (more in particular the skin-anode distance) is important for an accurate and correct administration of the X-ray radiation from the anode towards the target location within the anatomical portion to be treated.

Using the position and distance information for the miniature X-ray source also the operational parameters of the miniature X-ray source device for each target location are used in the treatment plan. These operational parameters contain information about the high voltage/current potentials to be applied to the miniature X-ray source device as well as the collimating setting value of the electrically controllable diaphragm lens element.

The pre-planned position and distance information parameters are used to control the movable robotic arm 210 in order to properly displace the miniature X-ray source device 10 to the corresponding actual positions and distances relative to the skin surface and anatomical portion to be treated.

Once the miniature X-ray source device 10 is positioned at an actual position/distance according the pre-planned parameters the actual radiation of the corresponding target location within the anatomical portion B is started. In order to verify whether the radiation treatment being actually performed conforms to the pre-planned treatment the actual position of the miniature X-ray source device 10 is being determined using the imaging means 260 and compared with the pre-planned position parameters.

In the event of any deviation the course of treatment can be adapted by controlling the robotic arm 210 (repositioning the X-ray source device) and by adapting the operational parameters of the X-ray source device.

The invention claimed is:

1. A miniature X-ray source device for effecting radiation therapy comprising:
   a vacuum tube containing a cathode and an anode spaced apart at some distance from each other, said cathode comprising an electron emitting material configured to emit free electrons;
   an electric field generating element configured to generate a high-voltage electric field between the cathode and the anode for accelerating the emitted free electrons towards the anode, and
   an exit window, wherein the anode is displaceable within the X-ray source device with respect to the exit window, wherein the cathode exhibits a concave shaped surface having a center part surrounded by an upright circumferential edge, and wherein the center part of the concave shaped surface is provided with said electron emitting material.

2. The miniature X-ray source device according to claim 1, wherein the center part of the concave shaped surface has a flat configuration.

3. The miniature X-ray source device according to claim 1, wherein the electron emitting material of the cathode is of a cold cathode type formed from carbon nanotubes.

4. The miniature X-ray source device according to claim 3, wherein the carbon nanotubes are aligned mono-wall nanotubes.

5. The miniature X-ray source device according to claim 3, wherein the carbon nanotubes are aligned multi-wall nanotubes.

6. The miniature X-ray source device according to claim 3, wherein the carbon nanotubes are randomised nanotubes.

7. The miniature X-ray source device according to claim 1, wherein a getter material is located in a high-voltage electric field free region in the vacuum tube.

8. The miniature X-ray source device according to claim 7, wherein the getter material is positioned within a groove present on the cathode.

9. The miniature X-ray source device according to claim 1, wherein the anode is provided with a flat X-ray emitting surface.

10. The miniature X-ray source device according to claim 9, wherein the anode is made from a first material, which material is at least partly transparent to X-ray radiation and wherein the anode is covered with a layer of a second material, which second material is at least partly non-transparent to X-ray radiation.

11. The miniature X-ray source device according to claim 10, wherein the second material is tungsten.

12. The miniature X-ray source device according to claim 10, wherein the layer of the second material has a thickness between 10 and 60 μm and preferably approximately 20 μm.

13. The miniature X-ray source device according to claim 1, wherein the vacuum tube further includes a diaphragm lens element disposed between the cathode and the anode for bundling the electrons emitted towards the anode.

14. The miniature X-ray source device according to claim 13, wherein the diaphragm lens element is electrically non-controllable.

15. The miniature X-ray source device according to claim 13, wherein the diaphragm lens element is electrically controllable.

16. The miniature X-ray source device according to claim 13, wherein the vacuum tube includes a grid shaped electron absorbing element disposed between the cathode and the diaphragm lens element, wherein the electron absorbing element is configured to absorb any electrons reflected from the diaphragm lens element towards the cathode.

17. The miniature X-ray source device according to claim 1, wherein the vacuum tube is at least partly made from an electrically isolating material.

18. The miniature X-ray source device according to claim 17, wherein the electrically isolating material is coated with a polymer layer.

19. The miniature X-ray source device according to claim 1, wherein the X-ray source device has a cylindrical shape with a diameter of 1-2.5 mm and a length of 2-3 cm.

20. The miniature X-ray source device according to claim 1, further including a cooling device configured to cool at least the anode.

21. The miniature X-ray source device according to claim 1, wherein the source device is mounted using a movable robotic arm of a therapy treatment system, the movement of the robotic arm being controlled by information generated by an imaging device and a therapy treatment planning device of the therapy treatment system.

22. The miniature X-ray source device according to claim 21, wherein the imaging device comprises a laser scanning device.

23. A method for performing radiation therapy treatment on an anatomical portion of an animal body using a miniature X-ray source device comprising:
   obtaining a three-dimensional image of the skin surface near said anatomical portion using an imaging means;
   determining, from the obtained three-dimensional image, the location of said anatomical portion relative to the skin surface;
   generating a radiation treatment plan for effecting said radiation therapy using a treatment planning means;
   displacing the miniature X-ray source device relative to the skin surface and the anatomical portion;
   determining, while performing radiation therapy treatment, the actual position of the miniature X-ray source device; and
   verifying the course of treatment with the treatment as pre-planned.

24. The method according to claim 23, wherein said treatment plan includes information concerning:
   the overall amount of radiation dose to be emitted to the anatomical portion;
   one or more target locations within the anatomical portion to be treated;
   the dose and the dwell time for each target location;
   the position of the miniature X-ray source device relative to each target location;
   the distance of the miniature X-ray source device relative to the skin surface for each position; and
   the operational parameters of the miniature X-ray source device for each target location.

25. The method according to claim 23, wherein the obtaining comprises:
   displaying said three-dimensional image of said target volume to an user using displaying means.

26. The method according to claim 23, wherein determining, the actual position comprises:
   determining the actual position of the miniature X-ray source device using said imaging means.

27. The method according to claim 23, wherein the obtaining comprises:
   placing one or more marker elements on the skin surface; and
   obtaining one or more three-dimensional images of the skin surface using these markers.

* * * * *

UNITED STATES PATENT AND TRADEMARK OFFICE
CERTIFICATE OF CORRECTION

PATENT NO. : 8,559,598 B2  Page 1 of 1
APPLICATION NO. : 12/665491
DATED : October 15, 2013
INVENTOR(S) : Kindlein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 699 days.

Signed and Sealed this
Fifteenth Day of September, 2015

Michelle K. Lee
*Director of the United States Patent and Trademark Office*